United States Patent

Jackson et al.

Patent Number: 5,723,663
Date of Patent: Mar. 3, 1998

[54] PREPARATION OF THIOAMIDES

[75] Inventors: Arthur Jackson, Washington; Graham Heyes; David Holmes, both of Durham; Craig Morgan, Billingham, all of England

[73] Assignee: Fine Organics, Ltd., England

[21] Appl. No.: 512,662

[22] Filed: Aug. 8, 1995

[30] Foreign Application Priority Data

Dec. 8, 1994 [GB] United Kingdom ............ 9416364

[51] Int. Cl.⁶ ............................................. C07C 333/02
[52] U.S. Cl. ........................................... 564/78; 564/74
[58] Field of Search .................................. 564/78, 74

[56] References Cited

U.S. PATENT DOCUMENTS

| | | | |
|---|---|---|---|
| 2,201,170 | 5/1940 | Hanford | 564/78 |
| 3,274,243 | 9/1966 | Gilbert et al. | 564/78 |
| 3,700,664 | 10/1972 | Girgis | 564/78 |

*Primary Examiner*—Richard J. Raymond
*Assistant Examiner*—Deborah Lambkin
*Attorney, Agent, or Firm*—Rodman and Rodman

[57] ABSTRACT

A process for preparing an aliphatic thioamide entails reacting a nitrile compound of the general formula $$R_1R_2R_3C\text{---}CN,$$

wherein $R_1$ denotes a hydrogen atom, an alkyl radical containing from 1 to 5 carbon atoms or an aryl radical and $R_2$ and $R_3$ each denotes a hydrogen atom containing from 1 to 5 carbon atoms, with hydrogen sulphide, in the presence as catalyst of an aliphatic amine of the general formula $$R_4R_5R_6N,$$

wherein $R_4$ denotes an alkyl radical containing 1 to 5 carbon atoms and $R_5$ and $R_6$ each denotes a hydrogen atom or an alkyl radical containing 1 to 5 carbon atoms, in a water-miscible polar solvent.

21 Claims, No Drawings

PREPARATION OF THIOAMIDES

The present invention is concerned with the preparation of thioamides, that is amides in which the oxygen atom is notionally replaced by a sulphur atom.

Thioamides, and in particular aliphatic thioamides, are of value as intermediates in the preparation of various products having a wide range of applications. By way of example, thioamides are useful in the preparation of thiazoles, many of which find application as pharmaceuticals. For these reasons, many different processes have been proposed for the preparation of thioamides.

The most widely practised process for this purpose entails reacting the corresponding amide with a suitable thiation agent, such as phosphorus pentasulphide or an aromatic derivative thereof known as Lawesson's Reagent. However phosphorus pentasulphide is a very difficult reagent to handle and the effluent obtained in the reaction is expensive to treat and dispose of. Lawesson's reagent is very expensive and also gives an effluent which entails disposal problems.

With a view to avoiding these foregoing difficulties, an alternative process has been proposed involving reacting a nitrile with hydrogen sulphide, to form the desired thioamide by direct addition of the hydrogen sulphide across the cyanide group. The reaction may be catalysed by amines. However, while this addition reaction gives good yields when applied to aromatic nitriles, aliphatic nitriles undergo reaction very slowly and give poor yields unless the reaction is carried out at elevated temperatures and pressures.

Against this background, it is an object of the present invention to provide a process for converting aliphatic nitriles to thioamides, by which improved reaction rates and/or improved yields of the desired product may be obtained even at ambient temperatures.

The process according to the present invention, for the preparation of aliphatic thioamides, comprises reacting a nitrile compound of the general formula

wherein the symbol $R_1$ denotes a hydrogen atom, an alkyl radical containing from 1 to 5 carbon atoms and the symbols $R_2$ and $R_3$ each denotes a hydrogen atom or an alkyl radical containing from 1 to 5 carbon atoms, with hydrogen sulphide, in the presence of an aliphatic amine of the general formula

wherein the symbol $R_4$ denotes an alkyl radical containing from 1 to 5 carbon atoms and the symbols $R_5$ and $R_6$ each denotes a hydrogen atom or an alkyl radical containing from 1 to 5 carbon atoms, in a water-miscible polar solvent.

The nitrile compound which is reacted in the process according to the invention is an aliphatic nitrile of the formula $R_1R_2R_3C$—CN, wherein the symbols $R_1$, $R_2$ and $R_3$ have the meanings given above. The alkyl groups may have straight or branched chains. Typical nitriles to which the reaction may be applied include acetonitrile, propionitrile, n- and isobutyronitrile and homologues of these foregoing compounds within the specified limits. Reaction of isobutyronitrile to yield thio-isobutyramide is of particular interest.

The reaction is catalysed by an aliphatic amine of the formula $R_4R_5R_6N$, wherein the symbols $R_4$, $R_5$ and $R_6$ have the meanings given above. By way of example, the catalyst may be methylamine, dimethylamine, ethylamine, n- or isopropylamine, di-isopropylamine or triethylamine. Of these, isopropylamine is particularly preferred. The quantity of the catalyst used is not critical but typically will be in the range of 10 to 100 mole percent in relation to the quantity of the nitrile. The preferred amount is in the range from 20 to 40 mole per cent.

The reaction is carried out in a water-miscible polar solvent, preferably an aprotic polar solvent, and such solvents are important in achieving acceptably high reaction rates. Suitable solvents for this purpose include dimethylacetamide, sulpholane, N-methylpyrrolidinone, 1,3-dimethylimidazolidinone and dimethyl sulphoxide. The particularly preferred solvent is dimethylformamide. The quantity of solvent is preferably in the range from 100 to 500g per mole of the nitrile, more preferably in the range from 120 to 300 g per mole of the nitrile.

The molar quantity of hydrogen sulphide preferably exceeds that of the nitrile and more preferably amounts to 110 to 300 mole per cent of the quantity of the nitrile. Typically, it amounts to 160 to 250 mole percent based on the nitrile.

The process according to the invention may be carried out under ambient conditions of temperature and pressure and makes possible good yields of the desired thioamide. However the reaction may, if desired, be accelerated and the yield enhanced by heating the reaction mixture to a temperature a little above the ambient temperature, for example to a temperature lying in the range from 30° C. to 50° C. preferably from 30° C. to 40° C.

The thioamide produced by the process may readily be separated from the reaction mixture by quenching with water and solvent extraction, for example using a solvent such as dichloromethane.

The invention will be further described and illustrated by means of the following examples.

EXAMPLE 1

To a stirred flask fitted with a condenser attached to a caustic scrubber were charged isobutyronitrile (100 g), isopropylamine (30 g), and dimethylformamide (400 ml). Hydrogen sulphide gas was charged to the vessel over a period of 24 hours and the reaction mixture stirred until the consumption of the nitrile became very slow.

The reaction mixture was quenched into water (900 ml) and extracted into dichloromethane (3×250 ml). The combined organic phases were dried with magnesium sulphate and then concentrated on a rotary evaporator, thereby yielding an oil which, apart from residual solvent, was essentially pure thio-isobutyramide (127 g, 85 percent yield).

EXAMPLE 2

A solution of isobutyronitrile (80 g) and isopropylamine (27.0 g) in dimethyl sulphoxide (125 ml) in a stirred reaction vessel fitted with a condenser was cooled to 0°–5° C. and connected to a caustic scrubber. A total of 85 g of hydrogen sulphide gas was added over 6 hours and the reaction mixture stirred until the reaction became very slow. Quenching into water (500 ml), extraction into dichloromethane (3×250 ml), followed by a small water backwash, yielded, on concentration, an oil which apart from residual solvent was essentially pure thioisobutyramide (yield 85 g, 71%).

EXAMPLE 3

Isopropylamine (54 g), propionitrile (128 g) and dimethylformamide (300 ml) were charged to a stirred reaction vessel fitted with a condenser attached to a caustic scrubber.

The mixture was cooled to 0°–5° C. and hydrogen sulphide gas charged over 24 hours, during which time the temperature was slowly allowed to rise to ambient temperature. After standing for a further 12 hours, the solution was concentrated under vacuum to 75% of its original volume, quenched into water (1600 ml) and then extracted with dichloromethane (3×250 ml). The combined organic phases were dried with magnesium sulphate and concentrated on a rotary evaporator to an oil which apart from residual solvent was essentially pure thiopropionamide (145 g, 70% yield).

EXAMPLES 4 TO 10

Using the reaction methods and separation techniques described in Examples 1 to 3, the nitriles set forth in the following table were reacted with hydrogen sulphide gas in the solvents shown, in the presence of the catalysts specified in the table. The yields of the corresponding thioamides are shown.

| Example | Nitrile | Solvent | Catalyst | Yield |
| --- | --- | --- | --- | --- |
| 4 | Isobutyronitrile | Dimethyl-formamide | Triethylamine | 89% |
| 5. | Isobutyronitrile | Dimethyl-formamide | Diethylamine | 78% |
| 6. | Isobutyronitrile | Sulpholane | Isopropylamine | 70% |
| 7. | Isobutyronitrile | Dimethyl-acetamide | Isopropylamine | 90% |
| 9. | Isobutyronitrile | 1,3-Dimethyl-imazolidinone | Isopropylamine | 72% |
| 10. | Phenylacetonitrile | Dimethyl-formamide | Isopropylamine | 70% |
| 10. | Trimethylacetonitrile | Dimethyl-formamide | Isopropylamine | 78% |

We claim:

1. A process for the preparation of an aliphatic thioamide, comprising reacting in a water miscible polar solvent, an aliphatic nitrile compound of the general formula:

$$R_1R_2R_3C\text{—}CN$$

wherein $R_1$, $R_2$ and $R_3$ each denotes a hydrogen atom or an alkyl radical containing from 1 to 5 carbon atoms, with hydrogen sulphide, in the presence of a catalytic amount of an aliphatic primary amine of the general formula:

$$R_4R_5R_6N$$

wherein $R_4$ denotes an alkyl radical containing from 1 to 5 carbon atoms and $R_5$ and $R_6$ each denotes a hydrogen atom.

2. A process according to claim 1, wherein the nitrile compound is selected from the group consisting of acetonitrile, propionitrile, n-butyronitrile, and isobutyronitrile.

3. A process according to claim 1, wherein the aliphatic amine is selected from the group consisting of methylamine, ethylamine, n-propylamine, and isopropylamine.

4. A process according to claim 1, wherein the water-miscible polar solvent is selected from the group consisting of dimethylformamide, dimethylacetamide, sulpholane, N-methylpyrrolidinone, 1,3-dimethylimazolidinone, and dimethyl sulphoxide.

5. A process for the preparation of an aliphatic thioamide, comprising reacting a nitrile compound selected from the group consisting of acetonitrile, propionitrile, n-butyronitrile, and isobutyronitrile with hydrogen sulphide, in the presence of a catalytic amount of an aliphatic primary amine selected from the group consisting of methylamine, ethylamine, n-propylamine, and isopropylamine, in a water-miscible polar solvent selected from the group consisting of dimethylformamide, dimethylacetamide, sulpholane, N-methylpyrrolidinone, 1,3-dimethylimazolidinone, and dimethyl sulphoxide.

6. A process according to claim 5, wherein the quantity of hydrogen sulphide lies within the range of 110 to 300 mole percent, based on the quantity of the nitrile compound.

7. A process according to claim 5, wherein the quantity of the aliphatic amine lies within the range of 20 to 40 mole percent, based on the quantity of the nitrile compound.

8. A process according to claim 5, wherein the quantity of solvent lies within the range from 100 grams to 500 grams per mole of the nitrile compound.

9. A process according to claim 5, wherein the reaction is carried out at a temperature lying in the range from 30° C. to 50° C.

10. A process according to claim 1, carried out under ambient conditions of temperature and pressure.

11. A process according to claim 1, wherein thioamide yields of about 70 to 90% are achieved.

12. A process according to claim 8. Wherein the quantity of solvent ranges from 120 grams to 300 grams per mole of the nitrile compound.

13. A process according to claim 6, wherein the quantity of hydrogen sulphide amounts to 160 to 250 mole percent based on the quantity of the nitrile compound.

14. A process according to claim 5, wherein the thioamide is separated from the reaction mixture by quenching with water and solvent extraction.

15. A process according to claim 14, wherein the solvent is dichloromethane.

16. A process according to claim 1, wherein the reaction is carried out at temperature in the range of 30° C. to 50° C.

17. A process for the preparation of thio-isobutyramide comprising reacting isobutyronitrile with hydrogen sulphide in the presence of isopropylamine, in solution in dimethylformamide.

18. A process according to claim 5 carried out under ambient conditions of temperature and pressure.

19. A process according to claim 5 carried out at ambient pressure and at ambient temperature or at a temperature in the range of from 30° C. to 50° C.

20. A process according to claim 1 carried out at ambient pressure and at ambient temperature or at a temperature in the range of from 30° C to 50° C.

21. A process according to claim 17 carried out under ambient conditions of temperature and pressure.

* * * * *

UNITED STATES PATENT AND TRADEMARK OFFICE
CERTIFICATE OF CORRECTION

PATENT NO. : 5,723,663
DATED : March 3, 1998
INVENTOR(S) : Jackson et al.

It is certified that error appears in the above-identified patent and that said Letters Patent is hereby corrected as shown below:

At Column 3, line 28, in the Table under the heading "Example" insert --8.--; under the heading "Nitrile" insert --Isobutyronitrile--; under the heading "Solvent" insert --N-methylpyrrolidinone--; under the heading "Catalyst" insert --Isopropylamine--; under the heading "Yield" insert --70%--.

UNITED STATES PATENT AND TRADEMARK OFFICE
CERTIFICATE OF CORRECTION

Page 2 of 2

PATENT NO. : 5,723,663
DATED : March 3, 1998
INVENTOR(S) : Jackson et al

It is certified that error appears in the above-identified patent and that said Letters Patent is hereby corrected as shown below:

At Column 3, line 31, in the Table under the heading "Example" delete "10"; under the heading "Nitrile" delete "Phenylacetonitrile"; under the heading "Solvent" delete "Dimethyl-formamide"; under the heading "Catalyst" delete "Isopropylamine"; under the heading "Yield" delete "70%".

Signed and Sealed this

Twenty-third Day of June, 1998

BRUCE LEHMAN

Attest:

Attesting Officer

*Commissioner of Patents and Trademarks*